(12) United States Patent
Németh et al.

(10) Patent No.: US 12,265,594 B2
(45) Date of Patent: Apr. 1, 2025

(54) DATA PROCESSING METHODS AND SYSTEMS FOR SIMULATING CHANGES TO CATEGORICAL FEATURES

(71) Applicant: Lynx Analytics Pte. Ltd., Singapore (SG)

(72) Inventors: András Németh, Budapest (HU); Dániel Darabos, Budapest (HU); Péter Erben, Budapest (HU); Dávid Herskovics, Budapest (HU)

(73) Assignee: Lynx Analytics Pte. Ltd., Singapore (SG)

( * ) Notice: Subject to any disclaimer, the term of this patent is extended or adjusted under 35 U.S.C. 154(b) by 445 days.

(21) Appl. No.: 17/734,194

(22) Filed: May 2, 2022

(65) Prior Publication Data

US 2022/0374654 A1 Nov. 24, 2022

(30) Foreign Application Priority Data

May 14, 2021 (SG) .............................. 10202105059R

(51) Int. Cl.
*G06F 18/214* (2023.01)
*G06T 7/10* (2017.01)
*G16H 50/20* (2018.01)

(52) U.S. Cl.
CPC .............. *G06F 18/214* (2023.01); *G06T 7/10* (2017.01); *G16H 50/20* (2018.01); *G06T 2207/20081* (2013.01)

(58) Field of Classification Search
CPC ...................... G06F 18/214; G06T 7/10; G06T 2207/20081; G16H 50/20; G06N 20/00
(Continued)

(56) References Cited

U.S. PATENT DOCUMENTS

2020/0250556 A1* 8/2020 Nourian .................. G06F 18/24

* cited by examiner

*Primary Examiner* — Stephen P Coleman
(74) *Attorney, Agent, or Firm* — Botos Churchill IP Law LLP

(57) ABSTRACT

Data processing method of simulating changes to categorical features of subjects are described. A method of simulating changes to categorical features of subjects comprises: receiving a current categorical feature set for the subject, the current categorical feature set for the subject comprising a plurality of categorical features for the subject, each categorical feature indicating a category from a plurality of possible categories into which the subject falls; inputting categorical features from the current categorical feature set for the subject into a set of trained machine learning models, each trained machine learning model of the set of trained machine learning model being configured to predict a respective outcome value for the subject from one or more of the categorical features for the subject, and thereby generating a set of current predicted outcome values for the subject; generating a plurality of simulated categorical features sets for the subject by varying respective categorical features for the subject; inputting categorical features from the simulated categorical feature sets for the subject into the set of trained machine learning models, and thereby generating a plurality of simulated sets of predicted outcome values for the subject; and storing a predicted outcome dataset for the subject, the predicted outcome dataset comprising the set of current predicted outcome values for the subject and the plurality of simulated sets of predicted outcome values for the subject.

27 Claims, 8 Drawing Sheets

(58) Field of Classification Search
USPC .......................................................... 382/103
See application file for complete search history.

| id | $l_1$ | $l_2$ | $max_1$ | $min_1$ | $cur_1$ | $l_1 \to a$ | $l_1 \to b$ | $l_1 \to c$ | $max_2$ | $min_2$ | $cur_2$ | $l_2 \to e$ | $l_2 \to f$ |
|---|---|---|---|---|---|---|---|---|---|---|---|---|---|
| 1 | b | e | 10 | 1 | 3 | 1 | 3 | 10 | 8 | 3 | 3 | 3 | 8 |
| 2 | c | e | 10 | 1 | 10 | 1 | 3 | 10 | 10 | 7 | 10 | 10 | 7 |
| 3 | c | f | 8 | 2 | 7 | 2 | 8 | 7 | 10 | 7 | 7 | 10 | 7 |

FIG. 6C

DATA PROCESSING METHODS AND SYSTEMS FOR SIMULATING CHANGES TO CATEGORICAL FEATURES

CROSS REFERENCE TO RELATED APPLICATIONS

The present application claims priority from Singapore patent application Ser. No. 10202105059R, filed May 14, 2021, the disclosure of which is incorporated herein by reference.

TECHNICAL FIELD

The present disclosure relates to data processing and in particular to simulating changes to categorical features of subjects.

BACKGROUND

Many organisations and businesses generate and have access to large amounts of data. This data may relate, for example to customers and customer activities. Certain information is known about these customers and their activities, such as their age, gender, location, what products and services they have signed up for and any issues that they have experienced recently. This information may be translated to categorical features for the customers. Categorical features indicate, for example, which age range a customer falls into or a range of services for which they have signed up. These categorical features may have an impact on outcomes for the business, for example a revenue or customer churn rate.

By conducting customer surveys and monitoring customer behaviour, it is possible to train machine learning models to predict outcomes from certain categorical features. However, the operation of such machine learning models can require a large amount of computational resources meaning that, for example, the simulation of changes to categorical features can be difficult to achieve in real time particularly when large amounts of data are involved.

SUMMARY

The present disclosure provides systems and methods for simulating changes to categorical features of subjects. The results of the simulation may be displayed in a dashboard which allows a user to analyze the potential impact of changes to the categorical features According to a first aspect of the present disclosure, a data processing method of simulating changes to categorical features of a subject is provided. The method comprises: receiving a current categorical feature set for the subject, the current categorical feature set for the subject comprising a plurality of categorical features for the subject, each categorical feature indicating a category from a plurality of possible categories into which the subject falls; inputting categorical features from the current categorical feature set for the subject into a set of trained machine learning models, each trained machine learning model of the set of trained machine learning model being configured to predict a respective outcome value for the subject from one or more of the categorical features for the subject, and thereby generating a set of current predicted outcome values for the subject; generating a plurality of simulated categorical features sets for the subject by varying respective categorical features for the subject; inputting categorical features from the simulated categorical feature sets for the subject into the set of trained machine learning models, and thereby generating a plurality of simulated sets of predicted outcome values for the subject; and storing a predicted outcome dataset for the subject, the predicted outcome dataset comprising the set of current predicted outcome values for the subject and the plurality of simulated sets of predicted outcome values for the subject.

According to a second aspect of the present disclosure a data processing method of simulating the impact of changes to categorical features of a plurality of subjects is provided. The method comprises: performing the method as set out above for a plurality of subjects; for a target outcome and a target categorical feature, determining an average current outcome value from the current predicted outcome values for the target outcome corresponding to respective subjects, determining a minimum average outcome value from the lowest value of the target outcome for each respective subject in the simulated set of predicted outcome values corresponding to the target categorical feature, and determining a maximum average outcome value from the highest value of the target outcome for each respective subject in the simulated set of predicted outcome values corresponding to the target categorical feature; calculating a potential impact of the target categorical feature on the target outcome from the maximum average outcome value and the minimum average outcome value; calculating an actual impact of the target categorical feature on the target outcome from the average current outcome value and the minimum average outcome value; and displaying an indication of the potential impact of the target categorical feature on the target outcome and an indication of the actual impact of the target categorical feature on the target outcome.

In an embodiment, the indication of the potential impact of the target categorical feature on the target outcome and the indication of the actual impact of the target categorical feature on the target outcome are displayed on a single chart.

In an embodiment, the indication of the potential impact of the target categorical feature on the target outcome is a ratio of the maximum average outcome value to the minimum average outcome value and the indication of the actual impact of the target categorical feature on the target outcome is a ratio of the average current outcome value to the minimum average outcome value or a ratio of the maximum average outcome value to the average current outcome value.

In an embodiment, the indication of the potential impact of the target categorical feature on the target outcome is a logarithm of the ratio of the maximum average outcome value to the minimum average outcome value and the indication of the actual impact of the target categorical feature on the target outcome is a logarithm of the ratio of the average current outcome value to the minimum average outcome value or a logarithm of the ratio of the maximum average outcome value to the average current outcome value.

In an embodiment, the method further comprises receiving an input indicating a selection of subjects and wherein the average current outcome value, the minimum average outcome value, and the maximum average outcome are determined for the selection of subjects.

In an embodiment, the method is carried out for a plurality of target categorical features.

In an embodiment, the method further comprises: calculating a group potential impact for a group of target categorical features on the target outcome from the respective potential impacts of the target categorical features making up the group on the target outcome; and calculating a group actual impact for the group of target categorical features on the target outcome from the respective actual impacts of the target categorical features making up the group on the target outcome; and displaying an indication of the group potential impact and the group actual impact.

According to a third aspect of the present disclosure, a data processing method of simulating changes to a categorical feature of a plurality of subjects is provided. The method comprises: receiving current categorical feature sets for each of a plurality of subjects, each current categorical feature set comprising a plurality of categorical features for a respective subject, each categorical feature indicating a category from a plurality of possible categories into which the respective subject falls; determining a current categorical feature distribution for a target categorical feature for the plurality of subjects, the current categorical feature distribution indicating a fraction of subjects falling into each category of the plurality of possible categories for the target categorical feature; inputting categorical features comprising the target categorical feature from the current categorical feature sets into a trained machine learning model configured to predict an outcome value for each subject from one or more of the categorical features for the subject, and thereby generating a current predicted outcome value for each subject; generating a plurality of simulated categorical feature sets for each subject by varying the target categorical feature; inputting categorical features from the simulated categorical feature sets into the trained machine learning model, and thereby generating a plurality of simulated sets of predicted outcome values; generating an aggregated simulated predicted outcome dataset from the plurality of simulated sets of predicted outcome values indicating the average predicted outcome for each possible variation in the target categorical feature; receiving an indication of a simulation target; determining a categorical feature distribution movement transformation from the current categorical feature distribution to a simulation categorical feature distribution which corresponds to a simulation outcome; determining a simulation result based on the simulation categorical feature distribution and/or the simulation outcome; and outputting an indication of the simulation result.

The simulation may be a forward simulation in which, the indication of the simulation target comprises an indication of a target distribution of categorical feature values and the simulation result is an outcome that results from target distribution of categorical feature values. Here, the simulation categorical feature distribution is the target distribution of categorical features and the simulation result is the simulation outcome.

Alternatively, the simulation may be a reverse simulation in which the indication of the simulation target comprises an indication of a target outcome value, and the simulation result is a categorical feature distribution that provides the target outcome. Here, the simulation outcome is the target outcome values and the simulation result is the simulation categorical feature distribution.

In an embodiment, wherein determining the categorical feature distribution movement transformation comprises determining a distribution movement transformation that gives a maximal simulated value, determining a distribution movement transformation that gives a minimal simulated value, determining a similarity measure between the simulation categorical feature distribution and each of the distribution resulting from applying the distribution movement transformation that gives a maximal simulated value to the current categorical feature distribution, the distribution movement transformation that gives a minimal simulated value to the current categorical feature distribution, and a unitary transformation to the current categorical feature distribution and thereby determining corresponding weights for the distribution movement transformation that gives a maximal simulated value, the distribution movement transformation that gives a minimal simulated value, and the unitary transformation.

In an embodiment, wherein the similarity measure is a cosine similarity measure.

According to a fourth aspect of the present disclosure a computer readable medium storing processor executable instructions which when executed on a processor cause the processor to carry out a method as set out above is provided.

According to a fifth aspect of the present disclosure a data processing system for simulating changes to categorical features of a subject is provided. The system comprises a processor and a data storage device storing computer program instructions operable to cause the processor to: receive a current categorical feature set for the subject, the current categorical feature set for the subject comprising a plurality of categorical features for the subject, each categorical feature indicating a category from a plurality of possible categories into which the subject falls; input categorical features from the current categorical feature set for the subject into a set of trained machine learning models, each trained machine learning model of the set of trained machine learning model being configured to predict a respective outcome value for the subject from one or more of the categorical features for the subject, and thereby generating a set of current predicted outcome values for the subject; generate a plurality of simulated categorical features sets for the subject by varying respective categorical features for the subject; input categorical features from the simulated categorical feature sets for the subject into the set of trained machine learning models, and thereby generating a plurality of simulated sets of predicted outcome values for the subject; and store a predicted outcome dataset for the subject, the predicted outcome dataset comprising the set of current predicted outcome values for the subject and the plurality of simulated sets of predicted outcome values for the subject.

In an embodiment, the data storage device further stores computer program instructions operable to cause the processor to: for a target outcome and a target categorical feature, determine an average current outcome value from the current predicted outcome values for the target outcome corresponding to respective subjects, determining a minimum average outcome value from the lowest value of the target outcome for each respective subject in the simulated set of predicted outcome values corresponding to the target categorical feature, and determining a maximum average outcome value from the highest value of the target outcome for each respective subject in the simulated set of predicted outcome values corresponding to the target categorical feature; calculate a potential impact of the target categorical feature on the target outcome from the maximum average outcome value and the minimum average outcome value; calculate an actual impact of the target categorical feature on the target outcome from the average current outcome value and the minimum average outcome value; and display an indication of the potential impact of the target categorical feature on the target outcome and an indication of the actual impact of the target categorical feature on the target outcome.

In an embodiment, the indication of the potential impact of the target categorical feature on the target outcome and the indication of the actual impact of the target categorical feature on the target outcome are displayed on a single chart.

In an embodiment, the indication of the potential impact of the target categorical feature on the target outcome is a ratio of the maximum average outcome value to the minimum average outcome value and the indication of the actual impact of the target categorical feature on the target outcome is a ratio of the average current outcome value to the minimum average outcome value or a ratio of the maximum average outcome value to the average current outcome value.

In an embodiment, the indication of the potential impact of the target categorical feature on the target outcome is a logarithm of the ratio of the maximum average outcome value to the minimum average outcome value and the indication of the actual impact of the target categorical feature on the target outcome is a logarithm of the ratio of the average current outcome value to the minimum average outcome value or a logarithm of the ratio of the maximum average outcome value to the average current outcome value.

In an embodiment, the data storage device further stores computer program instructions operable to cause the processor to: receive an input indicating a selection of subjects and wherein the average current outcome value, the minimum average outcome value, and the maximum average outcome are determined for the selection of subjects.

In an embodiment, the data storage device further stores computer program instructions operable to cause the processor to: carry out the method for a plurality of target categorical features.

In an embodiment, the data storage device further stores computer program instructions operable to cause the processor to: calculate a group potential impact for a group of target categorical features on the target outcome from the respective potential impacts of the target categorical features making up the group on the target outcome; and calculate a group actual impact for the group of target categorical features on the target outcome from the respective actual impacts of the target categorical features making up the group on the target outcome; and display an indication of the group potential impact and the group actual impact.

According to a sixth aspect of the present disclosure, a data processing system for simulating changes to a categorical feature of a plurality of subjects is provided. The system comprising a processor and a data storage device storing computer program instructions operable to cause the processor to: receive current categorical feature sets for each of a plurality of subjects, each current categorical feature set comprising a plurality of categorical features for a respective subject, each categorical feature indicating a category from a plurality of possible categories into which the respective subject falls; determine a current categorical feature distribution for a target categorical feature for the plurality of subjects, the current categorical feature distribution indicating a fraction of subjects falling into each category of the plurality of possible categories for the target categorical feature; input categorical features comprising the target categorical feature from the current categorical feature sets into a trained machine learning model configured to predict an outcome value for each subject from one or more of the categorical features for the subject, and thereby generating a current predicted outcome value for each subject; generate a plurality of simulated categorical feature sets for each subject by varying the target categorical feature; input categorical features from the simulated categorical feature sets into the trained machine learning model, and thereby generating a plurality of simulated sets of predicted outcome values; generate an aggregated simulated predicted outcome dataset from the plurality of simulated sets of predicted outcome values indicating the average predicted outcome for each possible variation in the target categorical feature; receive an indication of a simulation target; determining a categorical feature distribution movement transformation from the current categorical feature distribution to a simulation categorical feature distribution which corresponds to a simulation outcome; determine a simulation result based on the simulation categorical feature distribution and/or the simulation outcome; and output an indication of the simulation result.

In an embodiment, the indication of the simulation target comprises an indication of a target distribution of categorical feature values, the simulation categorical feature distribution is the target distribution of categorical features and the simulation result is the simulation outcome.

In an embodiment, the indication of the simulation target comprises an indication of a target outcome value, the simulation outcome is the target outcome values and the simulation result is the simulation categorical feature distribution.

In an embodiment, the data storage device further stores computer program instructions operable to cause the processor to: determine the categorical feature distribution movement transformation by determining a distribution movement transformation that gives a maximal simulated value, determining a distribution movement transformation that gives a minimal simulated value, determining a similarity measure between the simulation categorical feature distribution and each of the distribution resulting from applying the distribution movement transformation that gives a maximal simulated value to the current categorical feature distribution, the distribution movement transformation that gives a minimal simulated value to the current categorical feature distribution, and a unitary transformation to the current categorical feature distribution and thereby determining corresponding weights for the distribution movement transformation that gives a maximal simulated value, the distribution movement transformation that gives a minimal simulated value, and the unitary transformation.

In an embodiment, the similarity measure is a cosine similarity measure.

BRIEF DESCRIPTION OF THE DRAWINGS

In the following, embodiments of the present invention will be described as non-limiting examples with reference to the accompanying drawings in which:

FIG. 5 shows an example dashboard display for analyzing the impact of a categorical feature according to an embodiment of the present invention;

FIG. 6A to FIG. 6C are tables illustrating an example of simulating impact of categorical features using a method according to an embodiment of the present invention;

DETAILED DESCRIPTION

Figure 1:
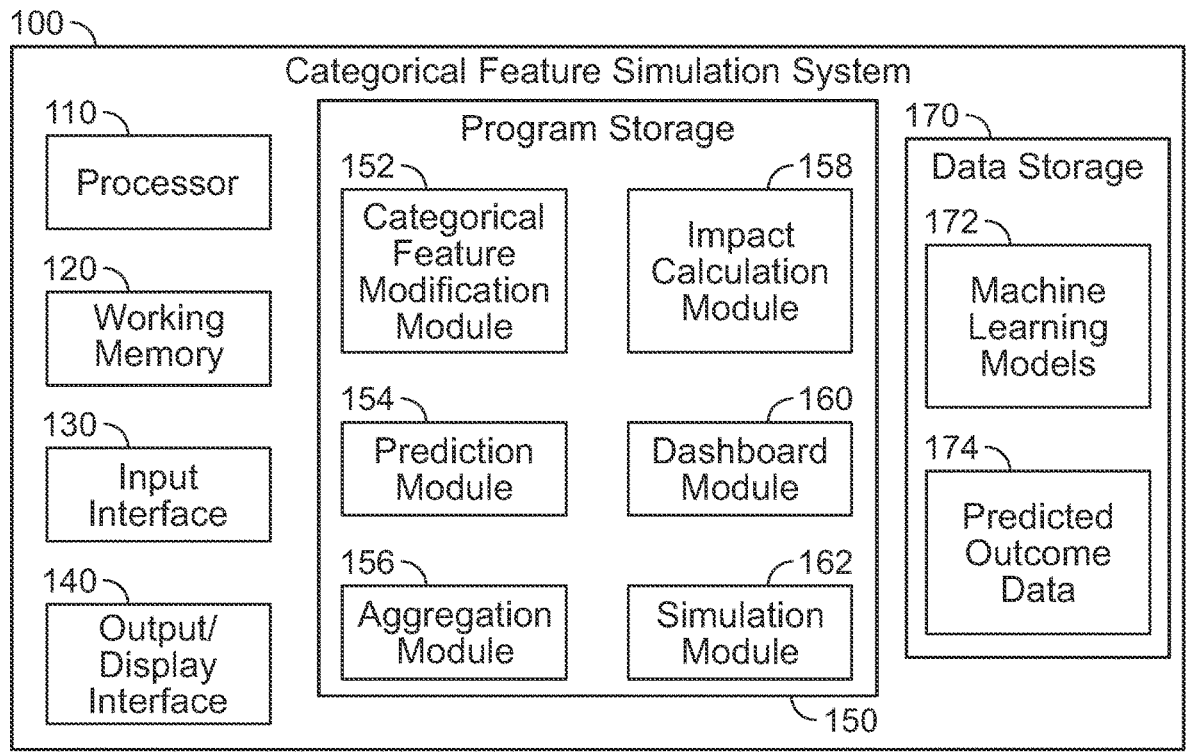
FIG. 1 is a block diagram showing a categorical feature simulation system according to an embodiment of the present invention.

The present disclosure relates to simulation of changes to categorical features of subjects and how these changes affect outcomes. The impact of changes to the categorical features on the outcomes may be displayed on a dashboard.

We describe subjects, which may for example be customers, with a finite set of categorical features. Each categorical feature has a finite set of possible values or categories which it may take. In the following description, the term ingredient is used interchangeably with categorical feature, and ingredient categories correspond to possible values or categories for the ingredients.

cat(I)={$v_1$, $v_2$, . . . } the set of possible categories for categorical feature I. In this document we assume that there are k categorical features: $I_1$, $I_2$, . . . , $I_k$.

In a customer-based implementation, such as a mobile telephone customer analysis scenario, the categorical features may be separated into "service quality categorical features": things that the operator has influence on, for example dropped calls, data speeds, call center waiting times, etc., and "context categorical features": things which are mostly out of control of the operator, such as demographic information for customers, competitor availability or social ingredients. In this document we assume we will support simulation for both type of categorical features (from the mathematical point of view there is no difference), but in actual implementations we may choose not to support simulation for context categorical features.

For subject (such as a customer) c the values of all the categorical features at a given time (for example, on a given day) form the categorical feature vector:

$\underline{x}_c = (x_1, x_2, \ldots, x_k)$, $x_j \in cat(I_j)$.

A set of subjects whose categorical feature vectors are known for a given time, is defined as a segment of subjects.

$\mathcal{S} = \{c_1, c_2, \ldots, c_n\}$

In the methodology described below, we often simulate changes by modifying some of the categorical feature values. The notation $\underline{x}[I \rightarrow v]$ means the categorical feature vector of which the value of categorical feature I is v, and all the other categorical features have the same value as in $\underline{x}$. If the value of I is v in $\underline{x}$, then $\underline{x}[I \rightarrow v] = \underline{x}$.

The list of ratios of the subject belonging to a category of the given categorical feature can be represented by a function:

$$D(v) = \frac{\text{number of subjects in category } v}{\text{total number of subjects}}$$

In the following description the typical use case will be that this D( ) distribution will be defined on a segment of subjects, such as a customer segment. But to keep the notation simple, we won't indicate the segment as a subscript or as a second parameter.

Outcomes are variables or values which may be of importance to decision makers. For example, expected probability of churn, customer lifetime value, average revenue per user (ARPU), net promoter score. We only deal with outcomes that can be defined on an individual level. These may then be aggregated on segments in various ways (typically sum or average), but it always has to start on the individual level. Outcomes need to be non-negative numbers. Can be "good" (like ARPU), if larger means better, or "bad" (like churn).

We can estimate outcomes both on individual level and for a segment of subjects. When the outcome is estimated on an individual level, we have a non-negative, real-valued function M( ) defined on the set of possible categorical feature vectors. The estimated outcome of subject c is $M(\underline{x}_c)$, where $\underline{x}_c$ is the categorical feature vector for the subject. We decided to always model expected values. For example, the expected number of churns for a customer is equal to the probability that the customer churns (in the next . . . days).

The M( ) function may be considered as a black box, because the dashboard doesn't have to know anything about M to work property.

With the above convention, we can speak about the expected/estimated outcome for a segment of subjects, because the expected value is additive.

$$\text{estimated outcome for segment } \mathcal{S} = CURR(\mathcal{S}) \sum_{c \in \mathcal{S}} M(\underline{x}_c)$$

The present disclosure provides a system that implements a dashboard page that can display these estimations for all the outcomes modelled.

If we want to display percentages on the dashboard, rather than total values, then the aggregation should be average instead of sum. For example:

$$\text{estimated churn ratio} = \frac{1}{|\mathcal{S}|} \cdot \text{estimated number of churners} =$$

$$\frac{1}{|\mathcal{S}|} \cdot \sum_{c \in \mathcal{S}} P(c \text{ churns}) = \frac{1}{|\mathcal{S}|} \cdot \sum_{c \in \mathcal{S}} M(\underline{x}_c)$$

Maximal and minimal estimations can be calculated. For a customer segment $\mathcal{S}$ and a fixed categorical feature I, we can compute, what would be the lowest and highest possible estimation, if all the subjects were in their best/worst categorical feature category of I. It is noted that the "best" and "worst" can be different for different subjects (because the other categorical feature values can be different for the subjects).

$$\text{MAX}(\mathcal{S}) = \sum_{c \in \mathcal{S}} \text{MAX}(c) = \sum_{c \in \mathcal{S}} \max_{v \in cat(I)} M(\underline{x}_c[I \rightarrow v])$$

$$\text{MIN}(\mathcal{S}) = \sum_{c \in \mathcal{S}} \text{MIN}(c) = \sum_{c \in \mathcal{S}} \min_{v \in cat(I)} M(\underline{x}_c[I \rightarrow v])$$

The lager the MAX($\mathcal{S}$)MIN($\mathcal{S}$) ratio, the higher the potential impact of I, because changes in I can have a big impact on the estimation. For "good" outcomes MAX corresponds to everyone being in their best category while for "bad" outcomes it corresponds to everyone being in their worst one.

The concept of categorical feature impact can be introduced which replaces the concept of score.

The potential categorical feature impact may be defined as the logarithm of the ratio of the maximum and minimum estimation for the segment $$\log_b\left(\frac{\text{MAX}(\mathcal{S})}{\text{MIN}(\mathcal{S})}\right)$$

The actual categorical feature impact indicates how much of the potential impact is realized currently.

$$\text{actual impact} = \begin{cases} \log_b\left(\frac{CURR(\mathcal{S})}{\text{MIN}(\mathcal{S})}\right) & \text{for "good" outcomes} \\ \log_b\left(\frac{\text{MAX}(\mathcal{S})}{CURR(\mathcal{S})}\right) & \text{for "bad" outcomes} \end{cases}$$

We use different formulas for "good" and "bad" outcomes so that on the dashboard a higher bar always means better. The usage of logarithm here is for scaling purposes. The b base of the logarithm can be any real number, greater than one. If b=2, then one unit improvement of the actual impact will always mean twice as good outcome (e.g., twice as much expected ARPU or half as much expected churn). Maybe a better choice for b is b=1.1, so that one unit improvement of the score means 10% increase of the estimation.

To make the dashboard more useful, we can simulate scenarios. Simulation means that we allow the user to say something about the possible change of the distribution of one or more categorical feature, and we compute or estimate the outcomes after the change. Its not feasible to define exactly, how all the categorical feature vectors change, this is why we only want to allow modifying ingredient distributions.

Two types of simulation are possible: (i) what impact does it have on the expected outcomes if we change the distribution of subjects in categories for a given categorical feature, and (ii) what impact does it have on the distribution of categorical feature categories and on the other expected outcomes if we directly change the actual impact (in context of an outcome O) of a given categorical feature.

We will call the first type (where we specify a distribution and compute an estimated impact) "forward simulation" and the second type (where we specify an impact level and compute the categorical feature distribution) "reverse simulation". The reverse simulation builds on the forward simulation in the following way. If we can estimate the outcome changes for the distribution of subjects, then we can choose a distribution that will change the outcome O as we want and then use the first type of simulation to estimate what will happen with the other outcomes. It is noted that there can be multiple suitable distributions for a desired change of an outcome, so we will need to define a choosing rule here. We might also want to simulate the change of several categorical features.

FIG. 1 is a block diagram showing a categorical feature simulation system according to an embodiment of the present invention. The categorical feature simulation system 100 is a computer system with memory that stores computer program modules which implement methods for simulating changes to categorical features according to embodiments of the present invention.

The categorical feature simulation system 100 comprises a processor 110, a working memory 120, an input interface 130, an output/display interface 140, program storage 150 and data storage 170. The processor 110 may be implemented as one or more central processing unit (CPU) chips. The program storage 150 is a non-volatile storage device such as a hard disk drive which stores computer program modules. The computer program modules are loaded into the working memory 120 for execution by the processor 150. The data storage 170 is a non-volatile storage device such as a hard disk drive which stores machine learning models and data. The input interface 130 is an interface which allows data including categorical feature data to be received by the categorical feature simulation system 100. The output/display interface 140 is coupled to an output device such as a display which allows the results of simulations to be displayed and analyzed. As described in more detail below, the output/display interface 140 may control a display to display a dashboard.

The program storage 150 stores a categorical feature modification module 152, a prediction module 154, an aggregation module 156, an impact calculation module 158, dashboard module 160 and a simulation module 162. The computer program modules cause the processor 110 to execute data processing which is described in more detail below. The program storage 150 may be referred to in some contexts as computer readable storage media and/or non-transitory computer readable media. As depicted in FIG. 1, the computer program modules are distinct modules which perform respective functions implemented by the categorical feature simulation system 100. It will be appreciated that the boundaries between these modules are exemplary only, and that alternative embodiments may merge modules or impose an alternative decomposition of functionality of modules. For example, the modules discussed herein may be decomposed into sub-modules to be executed as multiple computer processes, and, optionally, on multiple computers. Moreover, alternative embodiments may combine multiple instances of a particular module or sub-module. It will also be appreciated that, while a software implementation of the computer program modules is described herein, these may alternatively be implemented as one or more hardware modules (such as field-programmable gate array(s) or application-specific integrated circuit(s)) comprising circuitry which implements equivalent functionality to that implemented in software.

The data storage 170 stores machine learning models 172 and predicted outcome data 174. The machine learning models 172 are predictive models which are trained to take categorical features as input and to generate predicted outcome values based on the categorical features. The machine learning models 172 may comprise deep learning neural networks, decision trees and random forests, social graph models, and linear and logistic regression models.

Figure 2:
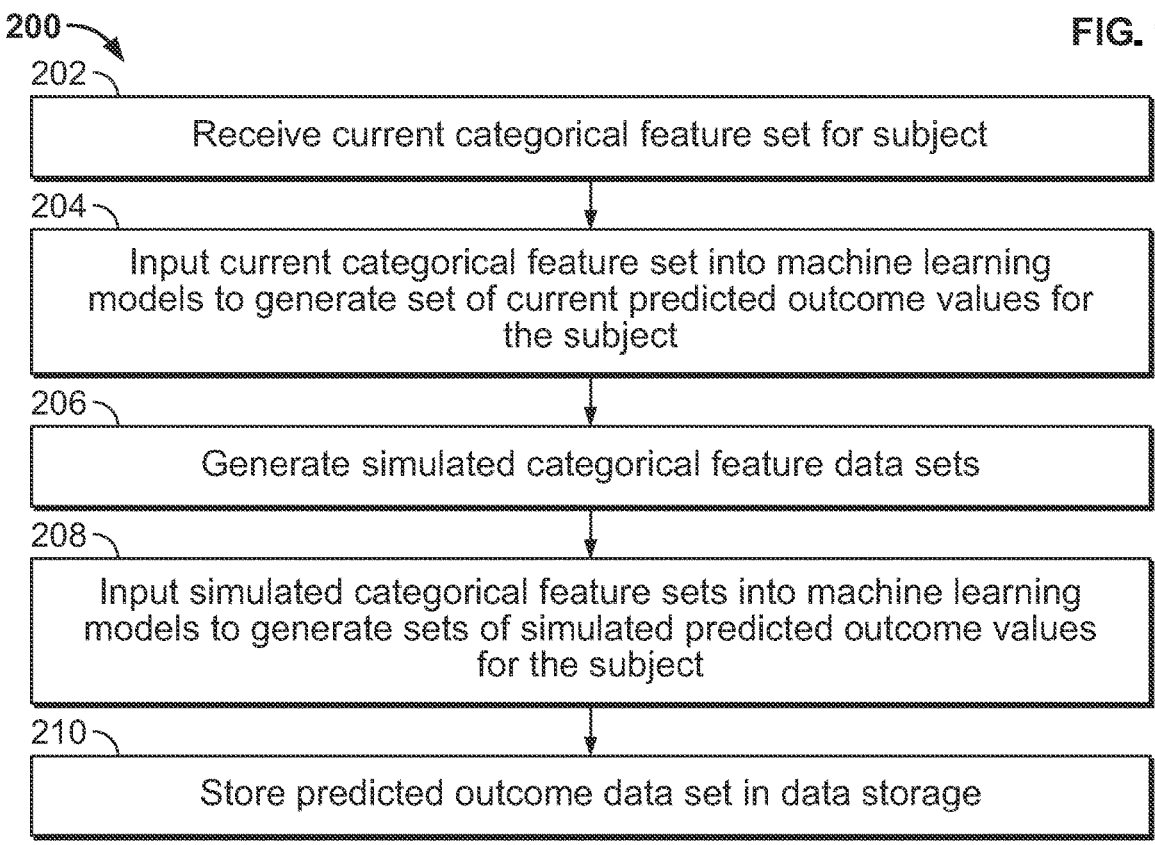
FIG. 2 is a flow chart showing a method of simulating changes to categorical features of a subject according to an embodiment of the present invention.

FIG. 2 is a flow chart showing a method of simulating changes to categorical features of a subject according to an embodiment of the present invention. The method 200 shown in FIG. 2 is carried out by the categorical feature simulation system 100 shown in FIG. 1.

In step 202, the input interface 130 receives a current categorical feature set for a subject. The current categorical feature set for the subject comprises a plurality of categorical features for the subject. Each categorical feature indicates a category from a plurality of possible categories into which the subject falls. As described above, the subject may be, for example, a customer and the current categorical feature set for the subject may comprise data on the customer's behavior and situation.

For example, a telephone company may monitor the number of calls made in the past 30 days for customers. This categorical feature may be categorized into three categories: 0-10 calls; 11-50 calls; and more than 50 calls.

In step 204, the prediction module 154 is executed by the processor 110 of the categorical feature simulation system 100 to input the current categorical feature set for the subject into the machine learning models 172 stored in the data storage 170. The machine learning models 172 generate a current set of predicted outcome values for the subject from the current categorical feature set for the subject. The predicted outcome may, for example be a lifetime revenue for a customer.

In step 206, the categorical feature modification module 152 is executed by the processor 110 of the categorical feature simulation system 100 to generate simulated categorical feature data sets by varying categorical features of the subject. The simulated categorical features are generated by changing the value of one of the categorical features for the subject. In an example, this comprises changing the number of calls made by the customer into the two categories other than the actual category for the customer while leaving the other categorical features for the subject unchanged.

In step 208, the prediction module 154 is executed by the processor 110 of the categorical feature simulation system 100 to input the simulated categorical features into the machine learning models 172 stored in the date storage 170. The machine learning models 172 generate sets of simulated predicted outcome values for the subject from the simulated categorical features sets for the subject. The simulated predicted outcome values, for example indicated the predicted lifetime revenue for the customer if a different number of calls were made in the 30-day period.

In step 210, predicted outcome date comprising the set of current predicted outcome values for the subject and the plurality of simulated sets of predicted outcome values for the subject are stored in the date storage 170 as predicted outcome data 174.

The method 200 shown in FIG. 2 may be repeated for a number of subjects and thus a large set of predicted outcome data 174 is generated and stored in the data storage 170. This predicted outcome data may be used to simulate the impact of changes to the categorical features of subjects on outcomes for the subject. Such a method is described below with reference to FIG. 3.

Figure 3:
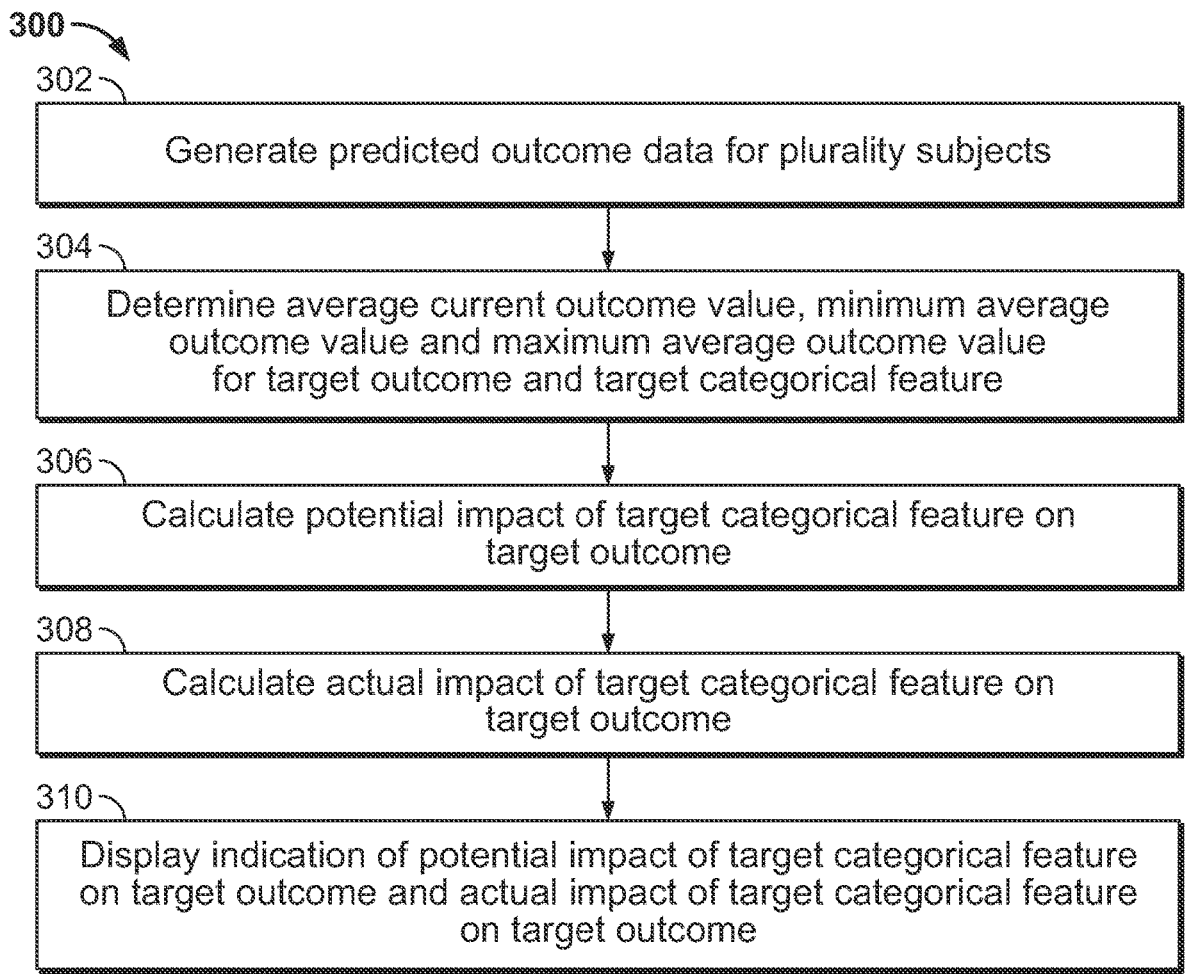
FIG. 3 is a flow chart showing a method of simulating the impact of changes to categorical features of a plurality of subjects according to an embodiment of the present invention.

FIG. 3 is a flow chart showing a method of simulating the impact of changes to categorical features of a plurality of subjects according to an embodiment of the present invention. The method 300 shown in FIG. 3 is carried out by the categorical feature simulation system 100 shown in FIG. 1.

In step 302, predicted outcome date is generated for a plurality of subjects. This is achieved by following the method 200 described above with reference to FIG. 2. The predicted outcome data 174 is stored in the data storage 170 of the categorical feature simulation system 100.

In step 304, the aggregation module 156 is executed by the processor 110 of the categorical feature simulation system 100 to determine outcome values for a target outcome and a target categorical feature. An average current outcome value is determined from the current predicted outcome values. A minimum average outcome value is determined from the lowest value of the target outcome for each respective subject in the simulated set of predicted outcome values corresponding to the target categorical feature. A maximum average outcome value is determined from the highest value of the target outcome for each respective subject in the simulated set of predicted outcome values corresponding to the target categorical feature.

For example, referring again to the telephone company example, the average predicted customer lifetime revenue based on current customer attributes may be $1,200. For each of a plurality of categorical features, it is determined how this value would change if the categorical features were varied. For example, for one customer, the current prediction is $2,000, the worst-case prediction is $800, and the best-case prediction is $3,000. In step 304, the best and worst cases for a given categorical features are averaged across all customers. For example, the worst-case average may be $500, and the best-case may be $2,000.

In step 306, the impact calculation module 158 is executed by the processor 110 of the categorical feature simulation system 100 to calculate the potential impact of the target categorical feature on the outcome. The potential impact is calculated as the difference between the maximum average outcome value and the minimum average outcome value achieved by varying the target categorical feature. In the example described above, the potential impact of the target categorical feature is $2,000−$500=$1,500. Thus, by varying the target categorical feature, the lifetime revenue can be varied by $1,500.

In step 308, the impact calculation module 158 is executed by the processor 110 of the categorical feature simulation system 100 to calculate the actual impact of the target categorical feature on the outcome. The actual impact is calculated from the difference between the average current outcome value and the minimum average outcome value. In the example described above, the actual impact is calculated as $1,200−$500=$700. This is how much higher the current value is compared to the worst-case scenario.

In step 310, the dashboard module 160 is executed by the processor 110 of the categorical feature simulation system 100 to cause the output/display interface 140 to display an indication of the potential impact of the target categorical feature on the target outcome and an indication of the actual impact of the target categorical feature on the target outcome. The indications of the potential impact and the actual impact may be displayed on a dashboard. An example of the display of indications of the potential impact and the actual impact is shown in FIG. 4.

Figure 4:
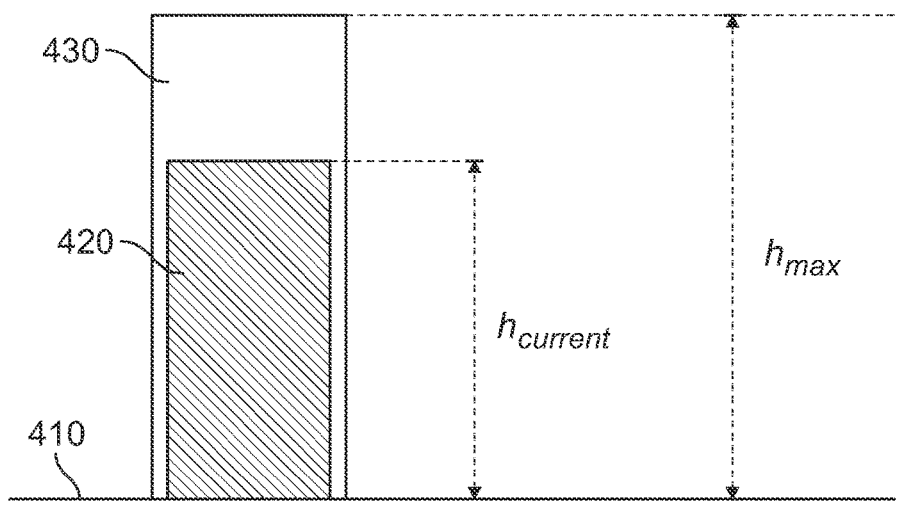
FIG. 4 shows an example dashboard display of an indication of a potential impact and an actual impact of a categorical feature on an outcome according to an embodiment of the present invention.

FIG. 4 shows an example dashboard display of an indication of a potential impact and an actual impact of a categorical feature on an outcome according to an embodiment of the present invention.

As shown in FIG. 4, the dashboard display shows the actual impact 420 and the potential impact 430 of a categorical feature in a single chart. The base level 410 is the minimum average outcome value, the height of the bar showing the actual impact 420 of the target categorical feature is the difference between average current outcome value and the minimum average outcome value and the height of the bar showing the potential image 430 of the target categorical feature is the difference between the maximum average outcome value and the minimum average outcome value. Thus, the values can be expressed by the following inequality.

$$h_{min}=0 \le h_{current}=\text{actual impact} \le h_{max}=\text{potential impact}$$

This methodology makes it easy to analyze the connections between business outcomes and a categorical feature regarding a given customer segment. We can visualize "categorical feature impact levels" by marking what would be the actual impact if every subject were in the same category of the categorical feature.

Figures 5, 6A, 6B:
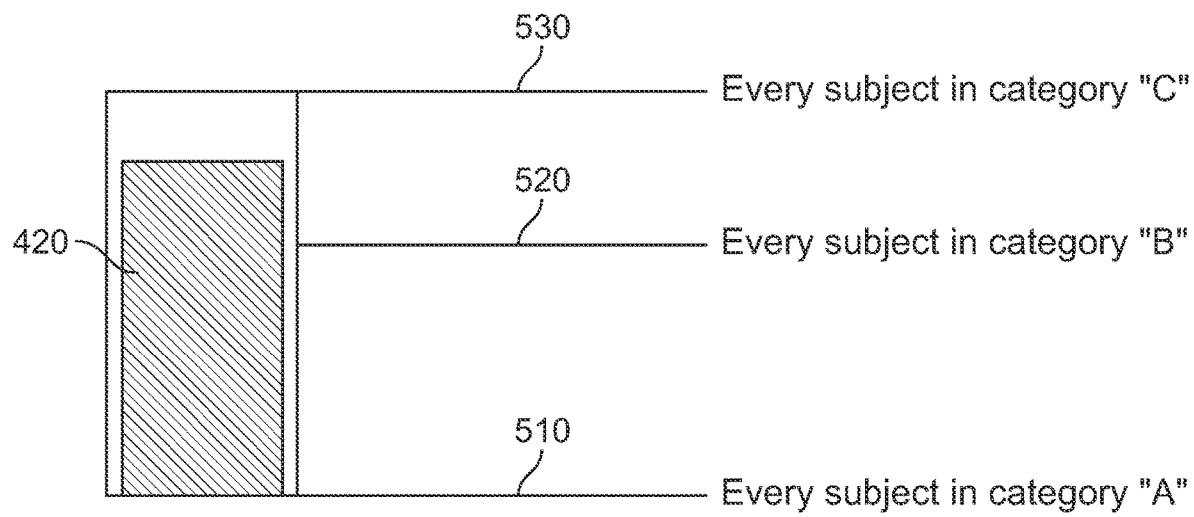

FIG. 5 shows an example dashboard display for analyzing the impact of a categorical feature according to an embodiment of the present invention. The dashboard display includes a line 510 marking what would be the actual impact if every subject were in category "A", a line 520 marking what would be the actual impact if every subject were in category "B", and a line 530 marking what would be the actual impact if every subject were in category "C". As can be seen in FIG. 5, the actual impact 420 is above the impact if every subject were in category "B", but below the impact if every subject were in category "C". It can happen that the "best" or the "worst" category is different for different customers, therefore it is not guaranteed that the "gray lines" of impact levels can reach the lowest or highest possible estimation for the segment.

In the following a simple example will be described. FIG. 6A to FIG. 6C are tables illustrating an example of simulating impact of categorical features using a method according to an embodiment of the present invention. In this example, we have two categorical features with possible values {a, b, c}, and {d, e} and the M( ) values (i.e. the outcome values) are shown in FIG. 6A. FIG. 6B contains a customer segment with the current categorical feature values.

Notice, that here the ordering of the $I_1$ categories depends on the value of $I_2$. Because of this there is no one "best" category for $I_1$, but there are different best ones per $I_2$ category.

For the dashboard we pre-compute some values which are stored in the data storage 170 as predicted outcome data 174. These values are shown in FIG. 6C. AS shown in FIG. 6C, there is a row for each subject. The columns $max_1$ and $min_1$ indicate the maximum and minimum outcome values from varying the categorical feature $I_1$. The column $cur_1$ indicates the outcome with the current value of categorical feature $I_1$. The next three columns indicate the results of changing the categorical feature $I_1$ to different possible values. Similarly, columns $max_2$ and $min_2$ indicate the maximum and minimum outcome values from varying the categorical feature $I_2$. The column $cur_2$ indicates the outcome with the current value of categorical feature $I_2$. The next two columns indicate the results of changing the categorical feature $I_2$ to different possible values.

The estimations and impact levels for $I_1$ are calculated as follows.

$$MIN_{I_1}(S)=1+1+2=4$$

$$MAX_{I_1}(S)=10+10+8=28$$

$$CURR(S)=3+10+7=20$$

$$M([I_1 \to a])=1+1+2=4$$

$$M([I_1 \to b])=3+3+8=14$$

$$M([I_1 \to c])=10+10+7=27$$

As can be seen from the above values, having all of the subjects in one category (in this case category c) does not cover the best (potential impact level). It is also worth noting that the order of the impact level lines can change from segment to segment FIG. 7 shows an example dashboard display of an indication of a potential impact and an actual impact of a categorical feature on an outcome according to an embodiment of the present invention based on the values shown in FIG. 6A to FIG. 6C.

Figure 7:
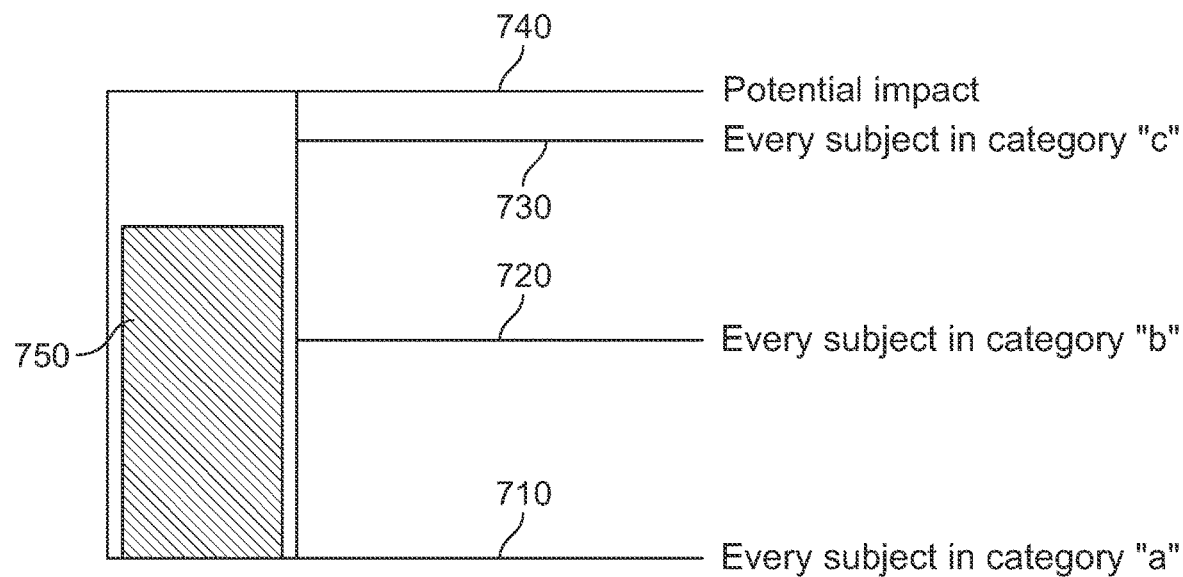
FIG. 7 shows an example dashboard display of an indication of a potential impact and an actual impact of a categorical feature on an outcome according to an embodiment of the present invention based on the values shown in FIG. 6A to FIG. 6C.

As shown in FIG. 7, the minimum average value 710 of the outcome occurs when every subject is in category "a". A line 720 indicates the average outcome value when every subject is in category "b", a line 730 indicates the average outcome value when every subject is in category "c". It is notable that the potential impact 740 is higher than the value when every subject is in category "c". In this example, the actual impact 750 is between the value when every subject is in category "b" and the value when every subject is in category "c".

In the examples described above, the dashboard display shows the impact of a single categorical feature on an outcome. Embodiments are envisaged in which the impact of multiple categorical features on an outcome are shown in the dashboard or the impact of multiple categorical features on different outcomes are shown.

Figure 8:
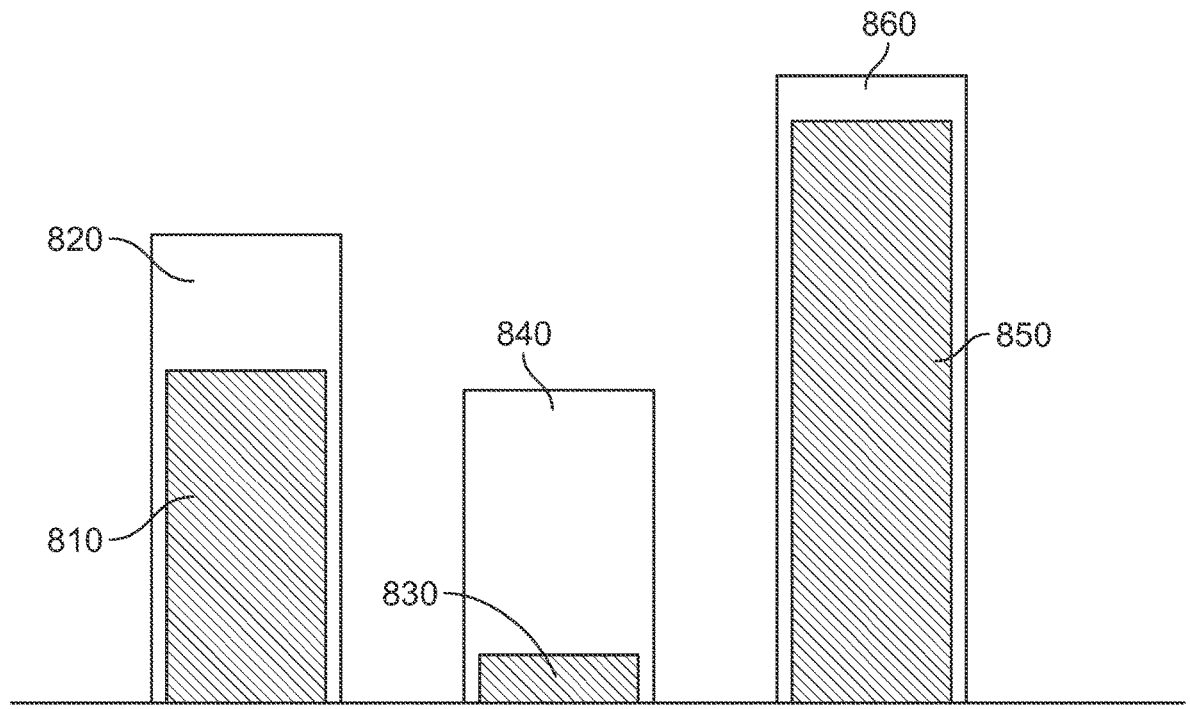
FIG. 8 shows an example dashboard display of indications of the potential impact and actual impact of multiple categorical features on an outcome according to an embodiment of the present invention.

FIG. 8 shows an example dashboard display of indications of the potential impact and actual impact of multiple categorical features on an outcome according to an embodiment of the present invention.

The dashboard display shown in FIG. 8 shows the impact of three categorical features on an outcome. A first categorical feature has an actual impact shown by a first actual impact indication 810 and a potential impact shown by a first potential impact indication 820. A second categorical feature has an actual impact shown by a second actual impact indication 830 and a potential impact shown by a second potential impact indication 840. A third categorical feature has an actual impact shown by a third actual impact indication 850 and a potential impact shown by a third potential impact indication 860. As can be seen from FIG. 8, the second categorical feature has a low potential impact, and the actual impact is below the potential impact. The third categorical feature has a high potential impact, and the actual impact is close to the potential impact. In some embodiments, categorical features and their respective impacts may be sorted and displayed in order of their actual or potential impacts.

In the examples described above, the absolute impacts are displayed and compared. In some embodiments, relative impacts may be displayed and compared, for example the impacts may be expressed as a percentage. Another way to represent the impact is to take the logarithm of the relative impact. The logarithmic impact is useful for two things. Firstly, it allows an impact score to be displayed so that a user can compare different categorical features without having to consider actual outcome value. Secondly, it can help to size the bars on the dashboard. For example, if an outcome is three times worst-case, and the best case would see it triple again, then in effect the current value is half way to the maximum. A logarithmic indication of the impact would reflect this and show a bar that is 50% filled.

In the examples described above, the impact is calculated for a single categorical feature. In some embodiments, the potential impact and actual impact are calculated for a group of target categorical features. The data storage 170 stores predicted outcome data 174 for each individual categorical feature. In order to make group level predictions calculations described above with reference to FIG. 3 are carried out for a group of categorical features, and the actual impact and potential impact of the group of categorical features may be displayed on the dashboard.

The categorical feature simulation system may also allow the user to simulate scenarios. This is possible in two different ways. Firstly, the user may adjust the distribution of subjects and then analyze the effect this has on the outcome. Secondly, the user may input an indication of an outcome and the system determines what change to the distribution of subjects is required to exhibit such a change in outcome. These two types of simulation may be termed forward simulation and reverse simulation respectively. In the following description, it is assumed that there is a single outcome and a single categorical feature selected for simulation.

Figure 9A:
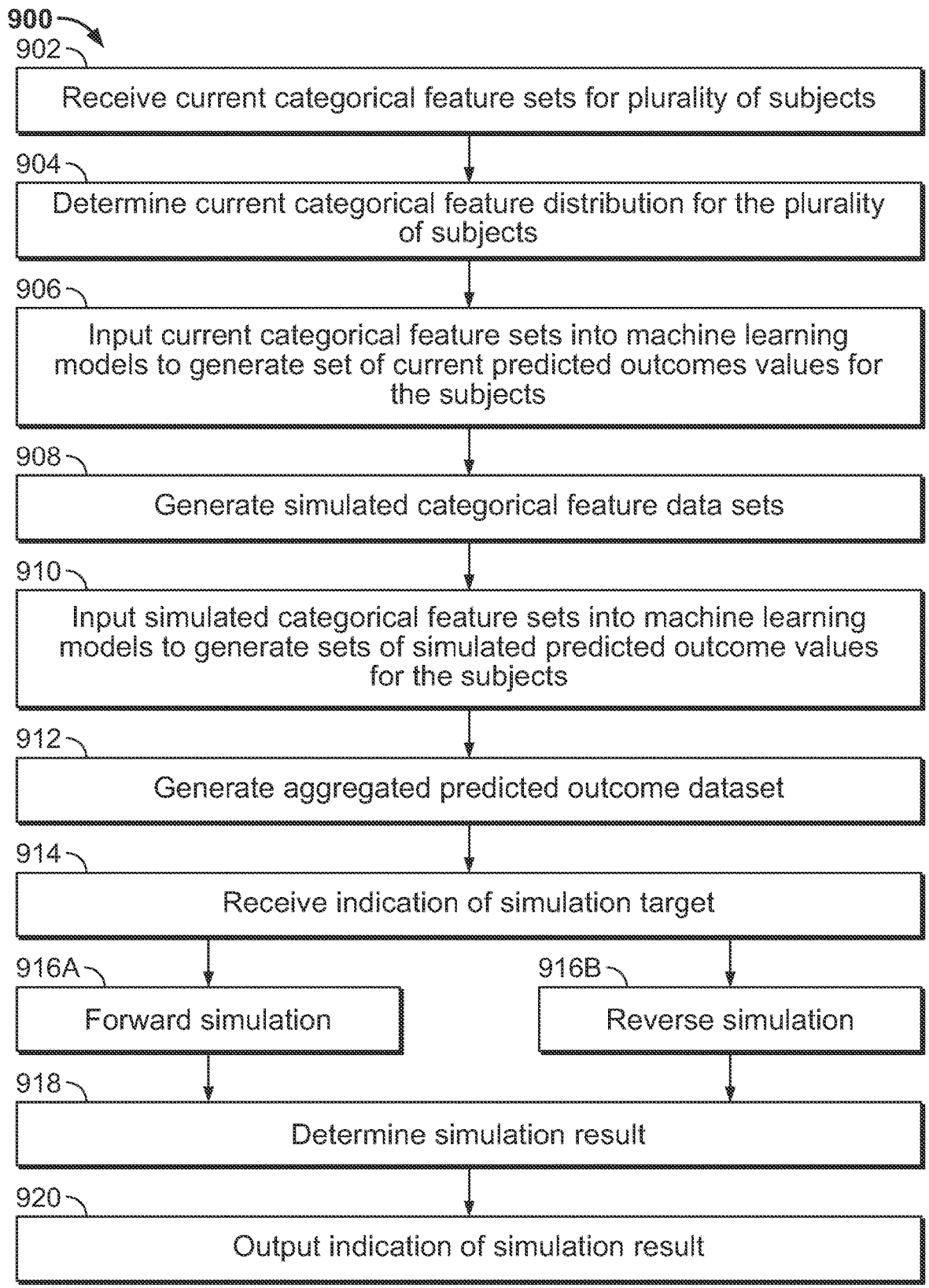
FIG. 9A to FIG. 9C are flow charts showing methods of simulating changes to a categorical feature of a plurality of subjects according to embodiments of the present invention.

FIG. 9A is a flow chart showing a method of simulating changes to a categorical feature of a plurality of subjects according to an embodiment of the present invention. The method 900 shown in FIG. 9A is carried out by the categorical feature simulation system 100 shown in FIG. 1.

In step 902, the input interface 130 of the categorical feature simulation system 100 receives current categorical feature sets for a plurality of subjects. Each current categorical feature set comprises a plurality of categorical features for each respective subject. The categorical features indicate a category from a plurality of possible categories into which the respective subject falls. The categorical feature set may correspond to the telephone company example described above with reference to FIG. 2.

In step 904, the aggregation module 156 is executed by the processor 110 of the categorical feature simulation system 100 to determine a current categorical feature distribution for the plurality of subjects. The distribution of a categorical feature is a k-dimensional real vector with non-negative coordinates, summing to one (assuming that the feature in question can have k distinct categorical values, $v_1$, $v_2, \ldots, v_k$). More formally, $\alpha$ is a distribution of the feature if and only if $$\alpha \in \mathcal{D}_k = \{(x_1, x_2, \ldots, x_k) | x_1 + x_2 + \ldots + x_k = 1, x_i \geq 0\}.$$

The number $x_i$ is the ratio of subject whose categorical feature has value $v_i$ if the distribution $\alpha$ is realized.

In step 906, the prediction module 154 is executed by the processor 110 of the categorical feature simulation system 100 to input current categorical feature sets into machine learning models to generate set of current predicted outcomes values for the subjects. From the categorical features the prediction of an outcome is calculated using the machine learning models 172. The list of feature values is denoted $f = (f_1, f_2, \ldots, f_n)$, and the predictive model is denoted by M( ).

$$\text{predictive outcome value} = M(f) = M(f_1, f_2, \ldots, f_n)$$

In step 908, the categorical feature modification module 152 is executed by the processor 110 of the categorical feature simulation system 100 to generate simulated categorical feature data sets by varying categorical features of the subjects. The simulated categorical features are generated by changing the value of one of the categorical features for the subject.

In step 910, the prediction module 154 is executed by the processor 110 of the categorical features simulation system 100 to input the simulated categorical feature sets into the machine learning models 172 to generate sets of simulated predicted outcome values for the subjects. The machine learning models 172 generate sets of simulated predicted outcome values for the subject from the simulated categorical features sets for the subject.

If a subject has feature vector f, we can define the set of "what-if" scenarios, for which for which the categorical feature simulation system 100 computes outcome predictions to support the simulation.

$$\text{what-if scenarios} = \{(g_1, g_2, \ldots, g_n) | \exists j : \forall_{i \neq j} g_i = f_i \wedge g_j \text{ is a value of the } j^{th} \text{ feature}\}$$

The data storage 170 stores the predictions for all what-if scenarios as predicted outcome data 174.

$$\text{what-if values} = \{M(g) | g \text{ is a what-if scenario}\}$$

In step 912, the simulation module 162 is executed by the processor 110 of the categorical feature simulation system 100 to generate an aggregated predicted outcome dataset. The aggregated predicted outcome dataset may take the form of a matrix. If one categorical feature is selected for the simulation and the possible categorical values of this feature have a fixed order $v_1, v_2, \ldots, v_k$ we can compress the predicted outcome data 174 into a "what-if" matrix $$W = (w_{i,j})$$

in the following way: $w_{i,j}$ is the average prediction for the subjects that currently have the feature value $v_i$ using the what-if scenario when they are put to category $v_j$. We can think about this matrix as an approximation, all the subjects in a segment are described by the same averages, which means that we lose information if we only use W for simulated outcome predictions.

In step 914, the categorical feature simulation system 100 receives an indication of a simulation target. The simulation target may be input by a user via the input interface 130 of the categorical feature simulation system 100.

As discussed above, there are two possible simulation types: a forward simulation and a reverse simulation.

If the simulation is a forward simulation, the indication of the simulation target comprises an indication of a target distribution and the method proceeds to step 916A in which the forward simulation is carried out. From the user's perspective the forward simulation takes a target distribution ($\beta \in \mathcal{D}_k$) and computes a simulated outcome value, assuming we know the current distribution ($\alpha \in \mathcal{D}_k$) and the what-if matrix for the selected ingredient (W).

$$\mathcal{F}_{\alpha, W}(\beta) = \text{simulated outcome value}$$

If the simulation is a reverse simulation, the indication of the simulation target comprises a target outcome value and the method proceeds to step 916B in which the reverse simulation is carried out. The reverse simulation takes a target outcome value in the allowed range $$s(\alpha, W, D_{min}) \leq o_{target} \leq s(\alpha, W, D_{max})$$

and computes a distribution $\gamma$ for which the forward simulation gives the simulated outcome value $o_{target}$. Here, s($\alpha$, W, D) is the simulated outcome value which is described in more detail below.

Figure 9B:
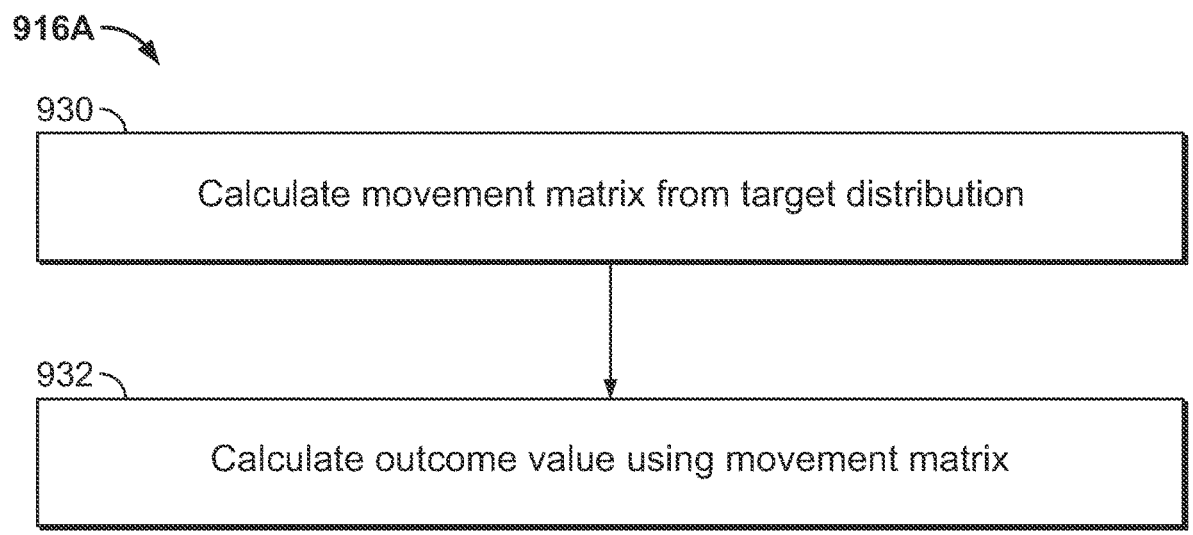

FIG. 9B is a flow chart showing a forward simulation method according to an embodiment of the present invention. The steps shown in FIG. 9B correspond to step 916A shown in FIG. 9A.

In step 930, the simulation module 162 is executed by the processor 110 of the categorical feature simulation system 100 to determine a categorical feature distribution movement transformation.

The categorical feature distribution movement transformation may be termed a "movement matrix". The simulation deals with feature distributions. We have the actual distribution of a feature and we have a "target" distribution. The simulation algorithm chooses a "movement matrix" $D=(d_{i,j})\in (\mathcal{D}_k)^k$ to realize the target distribution. This movement matrix describes what percentage of the subjects currently in category $v_i$ "will be moved" to category $v_j$. When we start the simulation, the movement matrix is equal to the k×k-dimensional unit matrix, meaning that each subject is in its current category. The main part of the simulation logic is about finding a proper movement matrix given the original distribution and the target distribution. We denote the movement matrix by D because the rows of this matrix are distributions.

If we have the original distribution $\alpha=(x_1, x_2, \ldots, x_k)$, the what-if matrix $W=(w_{I,j})$ and the movement matrix $D=(d_{i,j})$, we compute the simulated outcome value as follows:

$$\text{simulated outcome value} = s(\alpha, W, D) = \sum_i x_i \cdot \sum_j d_{i,j} \cdot w_{i,j}$$

This formula can be interpreted as follows. Originally a subject is in category $v_i$ with probability $x_i$. The simulation moves these subjects (that are in $v_i$) to category $v_j$ with probability $d_{i,j}$. The average predicted outcome for customers who are originally in $v_i$ and moved to $v_j$ is $w_{I,j}$. So the above formula is the expected average prediction in the simulated scenario, with the simplification of using per segment averages instead of individual level what-if values.

The algorithm which implements the forward simulation first creates a movement matrix $m(\alpha, \beta, W)=D$ for $\beta$ then returns $s(\alpha, W, D)$ as the simulated outcome value.

$$\mathcal{F}_{\alpha,W}(\beta)=s(\alpha,W,m(\alpha,\beta,W))$$

In the choice of D the algorithm has a great freedom since there are infinitely many movement matrices which produce the target distribution (but while these different movement matrices produce the same target distribution, they produce different outcome predictions). We use this freedom to maximize the range of outcome values which can be reached by the simulation.

The movement matrix defines what fraction of the customers in category $v_i$ will be moved to category $v_j$. If the current distribution is $\alpha=(x_1, x_2, \ldots, x_k)$ and the movement matrix is $d_{i,j}$, then the simulated distribution is $$fl_\alpha(D) = \alpha D = \left(\sum_i x_i \cdot d_{i,1}, \sum_i x_i \cdot d_{i,2}, \ldots, \sum_i x_i \cdot d_{i,k}\right).$$

The name of the function fl comes from "flatten".
There are three scenarios for which the corresponding movement matrix is known.
(I) The current distribution corresponds to the unit matrix, $\alpha D=\alpha \Leftrightarrow D=I$.
(II) If the target distribution is such that one coordinate (i.e. the $j^{th}$) is 1, all the others are zero, then the only possible movement matrix is the one which has all ones in its $j^{th}$ column, and zeros everywhere else.
(III) Using s( ) for the forward simulation we can tell which movement matrix gives the maximal and which gives the minimal simulated value. These matrices are unique if the elements of W are different. To get these movement matrices we pick the maximal (minimal) element in each row of W and write 1 to that position, and zero everywhere else. These special movement matrices (assuming they are unique) are called $D_{max}$ and $D_{min}$.

A given movement matrix D determines a feature distribution $fl_\alpha(D)$. This distribution is not equal to $\beta$ (the target distribution) for most movement matrices. The simulation algorithm uses a transformation to get another movement matrix D' from D which is "as close as possible" to D and determines $\beta$.

$$cm(D)=D' \Rightarrow fl_\alpha(D')=\beta \wedge D' \text{ is close to } D$$

The concept of "closeness" is not defined formally. We use an algorithm which only changes the elements of the original movement matrix if necessary and tries to keep as much of the distributions in the diagonal as possible.

A more detailed description of the algorithm is as follows. The algorithm starts with a copy C of D. It compares the target distribution $\beta$ to $fl_\alpha(C)$ and adjusts elements of C depending on the sign of the coordinates of $fl_\alpha(C)-\beta$. We use the term source for row indexes and the term destination for the column indexes of a movement matrix.

Step 1: We handle destinations where the $fl_\alpha(C)$ is greater than $\beta$. We compute the final values for all these columns (for all sources) and save the "overflow".

Step 2: For the other columns we first look at the diagonal and put as much of the "overflow" there as we can fit.

Step 3: In the columns that are still not satisfied (meaning $fl_\alpha(C)$ is still less than $\beta$), we distribute the remaining overflow evenly.

Figure 10A:
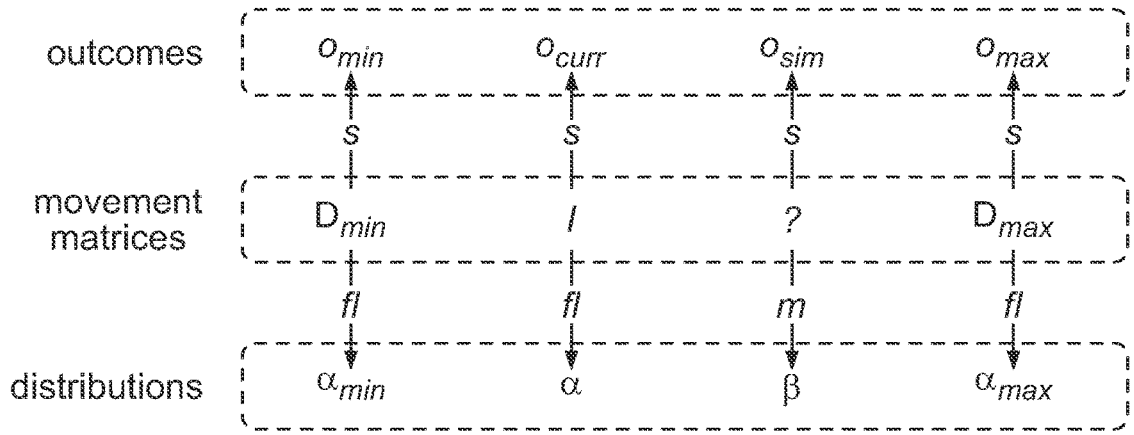
FIG. 10A and FIG. 10B are flow diagrams showing the determination of categorical feature movement matrices in embodiments of the present invention.
Figure 10B:
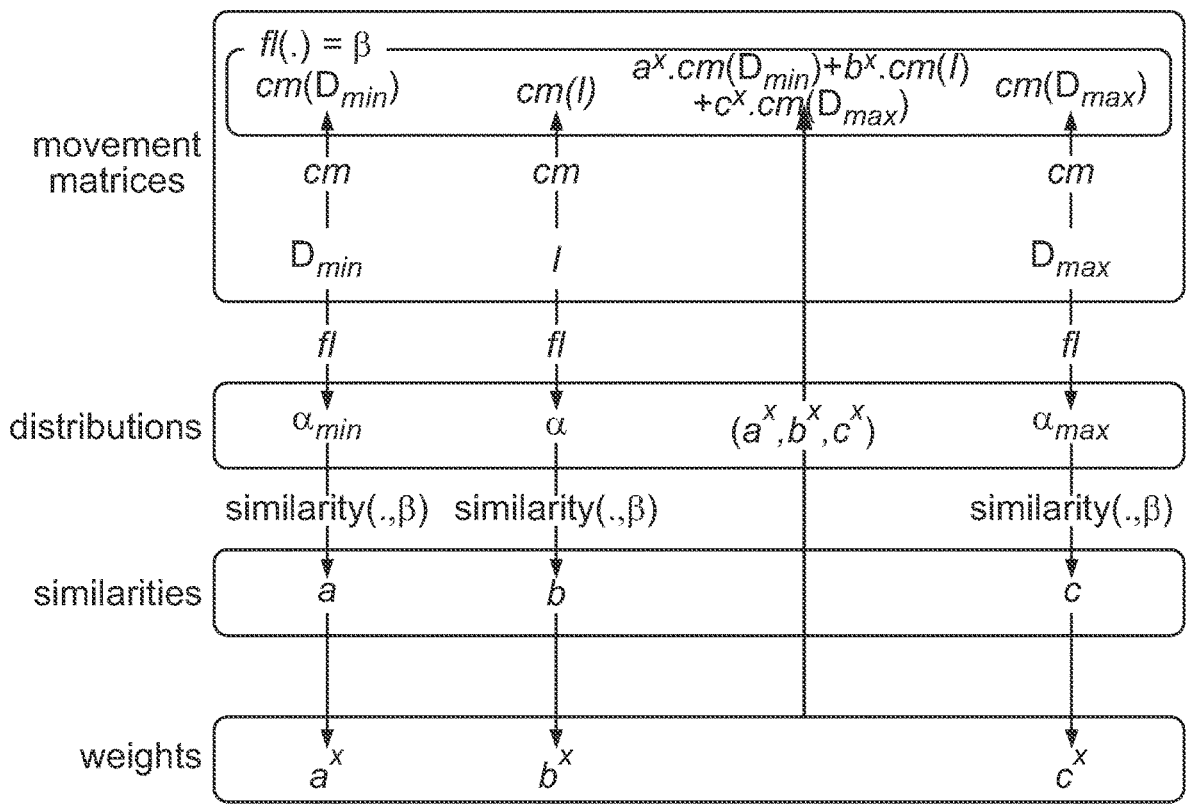

A high-level overview of the algorithm will now be described with reference to FIG. 10A and FIG. 10B. FIG. 10A and FIG. 10B are flow diagrams showing the determination of categorical feature movement matrices in embodiments of the present invention.

Compute $D_{min}$ and $D_{max}$ to get the range of possible simulated values.

Compute $\alpha_{min}=fl_\alpha(D_{min})$ and $\alpha_{max}=fl_\alpha(D_{max})$.

Determine "how close" (or "how similar") the target distribution $\beta$ is to $\alpha_{min}$, $\alpha$ and $\alpha_{max}$.

Compute weights from the above "closeness" measures. The weight-computation ensures that if the target distribution is identical to one of to $\alpha_{min}$, $\alpha$ or $\alpha_{max}$ then only that weight will be non-zero which corresponds to the identical distribution.

Return the weighted element-wise average of $cm(D_{min})$, $cm(I)$ and $cm(D_{max})$. Because cm( ) transforms any movement matrix to one which flattens to $\beta$, the returned matrix also has this property.

We define the "closeness" (or "similarity") of two distributions by using cosine-similarity. This is a commonly used similarity measure for feature vectors.

$$\alpha(x_1, \ldots, x_k), \beta(y_1, \ldots, y_k) \in \mathcal{D}_k \Rightarrow \text{similarity } (\alpha, \beta) = \frac{\Sigma x_i \cdot y_i}{\sqrt{\Sigma x_i^2} \cdot \sqrt{\Sigma y_i^2}}$$

This similarity measure is generally between −1 and 1, but for distributions it is always non-negative and it is equal to 1 if and only if the two distributions are identical. (The similarity measure is 0 when the two distribution vectors are orthogonal in the k-dimensional space but this interpretation is less useful in the present context).

Three similarity measures are calculated:

$a=sim_{min}=\text{similarity}(\alpha_{min},\beta)$, $b=sim_{curr}=\text{similarity}(\alpha,\beta)$, $c=sim_{max}=\text{similarity}(\alpha_{max},\beta)$, Then, weights are defined such that higher similarity means bigger weight, and in the special case when exactly one similarity is 1, the corresponding weight should be 1, and the others should be zero.

Our approach is to use binary search to find an approximated solution of the equation $a^x+b^x+c^x=1$ in the range $x \in [2^{-M}; 2^M]$ and use $a^x$, $b^x$, and $c^x$ as weights. M should be a big enough integer so that $2^{-M}$ is close enough to zero, but $2^M$ is still representable in the programming language of the implementation.

In the special case a=b=c=0 we simply define all the weights to be ⅓ without running the binary search. This makes sense because in that case the target distribution is not similar to any of our "special" distributions so it is reasonable to use equal weights.

When a+b+c=1 then x=1 is a solution and we should get back (a, b, c).

When all the similarity measures are strictly between zero and one (0<a, b, c<1), then $$\lim_{x \to +0} g(x) = 3 \text{ and } \lim_{x \to +\infty} g(x) = 0,$$

so using the fact that g(x) is continuous on the given range, the binary search gives us a good approximation of the solution. (In this case the equation has a unique real solution in the range [0; +∞] because all three terms are monotonic in x).

When exactly one of a, b, c is 1 and another one is positive, then we have a similar situation but the limits are different:

$$\lim_{x \to +0} g(x) = 2 \text{ and } \lim_{x \to \infty} g(x) = 1,$$

but the binary search will still give us a sufficient x if M is large enough. (Sufficient here means that one weight will be 1 and the other two will be very close to 0).

It is noted that for equal similarity measures the method computes equal weights and as a consequence we get a meaningful result even if more than one similarity measure is 1.

When the binary search stops, $a^x+b^x+c^x$ may differ from 1 because we use a limited range for x and we also limit the number of steps the search can take (and because there are inputs for which there is no real (finite) solution). To provide proper weights for the later steps of the algorithm, we normalize the values to have 1 as sum:

$$(a^x, b^x, c^x) \to \left(\frac{a^x}{a^x+b^x+c^x}, \frac{b^x}{a^x+b^x+c^x}, \frac{c^x}{a^x+b^x+c^x}\right),$$

but for the sake of simplicity we will refer to the returned weights in this document as simply $(a^x, b^x, c^x)$. If the binary search gave us a precise enough weight tuple then this last step does not change the values.

Returning to the movement matrix:

$$D^* = a^x \cdot cm(D_{min}) + b^x \cdot cm(I) + c^x \cdot cm(D_{max}).$$

It can be proven that this is indeed a movement matrix as follows. Assume that $D_i$ is a movement matrix for $i \in \{1,2,3\}$ and $0 \leq w_i \in R$, $\Sigma_{i=1}^{3} w_i = 1$. We will show that $D = \Sigma w_i D_i$ is a movement matrix. Because $D_i$ is a movement matrix and the weights are non-negative, all the elements of D are non-negative. It remains to be proved that all the row sums of D are equal to 1. It follows from the fact that if sum of the $j^{th}$ row of $D_i$ is $s_{j,i}$, then the sum of $j^{th}$ row of D is equal to $\Sigma_i w_i \cdot s_{i,j} = \Sigma_i w_i \cdot 1 = \Sigma_i w_i = 1$.

From the definition of cm( ) it follows that $fl_\alpha(D^*)=\beta$, and our algorithm gives back D if $\beta=\alpha$. It can also be seen, that we get back $D_{max}$ and $D_{min}$ for the target distributions $fl_\alpha(D_{max})$ and $fl_\alpha(D_{min})$, so in a sense our algorithm covers the widest possible simulation range.

In step 932, the simulation module 162 is executed by the processor 110 of the categorical feature simulation system 100 to calculate the outcome value using the movement matrix calculated as described above.

Figure 9C:
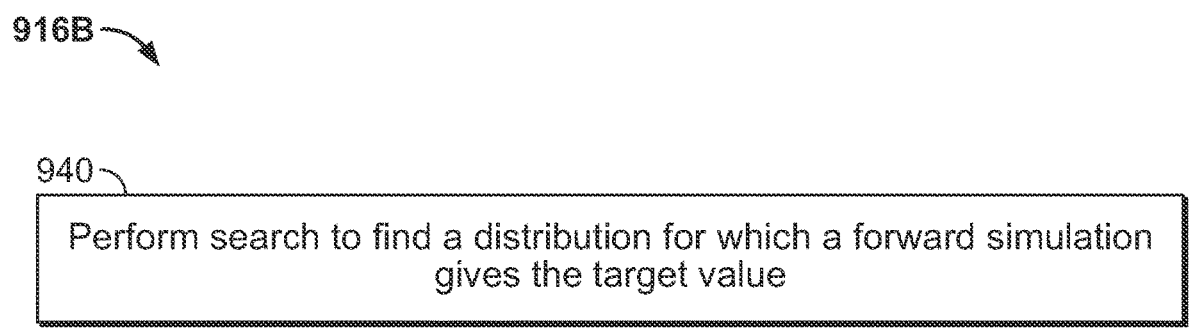

FIG. 9C is a flow chart showing a reverse simulation method according to an embodiment of the present invention. The step shown in FIG. 9C correspond to step 916B shown in FIG. 9A. The reverse simulation gets a target outcome value in the allowed range $$s(\alpha, W, D_{min}) \leq o_{target} \leq s(\alpha, W, D_{max})$$

and computes a distribution γ for which the forward simulation gives the simulated outcome value $o_{target}$.

As shown in FIG. 9C, in step 940, the simulation module 162 is executed by the processor 110 of the categorical feature simulation system 100 to perform a search to find a distribution for which a forward simulation gives the target value.

The core idea is that if $o_{min} \leq o_{target} \leq o_{current}$, then we express γ as a linear combination of $\alpha_{min}$ and α, and when $o_{current} \leq o_{target} \leq o_{max}$ then we look for a linear combination of α and $\alpha_{max}$. Our function s( ) is continuous in the target distribution so we can use binary search to find a proper γ.

The binary search is run on the range [−1; 1] and for a value $\lambda \in [-1; 1]$ we use the linear combination of distributions as below:

$$\text{distribution to try} = \begin{cases} (1-\lambda) \cdot \alpha + \lambda \cdot \alpha_{max} & \text{if } \lambda > 0 \\ (1-|\lambda|) \cdot \alpha + |\lambda| \cdot \alpha_{min} & \text{if } \lambda \leq 0 \end{cases}$$

As we can see λ=−1 maps to $\alpha_{min}$, λ=0 maps to α and λ=1 maps to $\alpha_{max}$.

Returning now to FIG. 9A, in step 918, the simulation module 162 is executed by the processor 110 of the categorical feature simulation system 100 to determine the simulation result. If the simulation is a forward simulation, then the simulation result is a simulated outcome value. If the simulation is a reverse simulation then the simulation result is a distribution of categorical feature values. The simulation result is determined using the methods discussed above.

In step 920, the output/display interface 140 of the categorical feature simulation 100 system outputs an indication of the simulation result.

In the description above, it was assumed that a single feature was selected for the simulation and we provided an algorithm which creates a mapping between target distributions and outcome predictions.

In some embodiments, the categorical feature simulation system 100 also allows changing multiple feature distribution at the same time. If the user decides to change multiple distributions, the algorithm produces an outcome prediction using the following logic.

Step 1. First it runs the simulation independently on all features involved.

Step 2. It returns an aggregated value, computed from the individual predictions, using a predefined aggregation method.

By default, we assume that all the outcome predictions are positive numbers and we use a "multiplicative" model for the aggregation:

$$\text{aggregated prediction} = \text{current prediction} \cdot \prod_{f \in \{changed\ features\}} \frac{\text{simulated prediction for } f}{\text{current prediction}}$$

The motivation behind this approach is that if we assume a probabilistic outcome and add a couple of independence assumptions then we formally get this formula as the proper aggregation. If the positivity or the independence assumption is not realistic, the aggregation method can be customized.

Whilst the foregoing description has described exemplary embodiments, it will be understood by those skilled in the art that many variations of the embodiments can be made within the scope and spirit of the present invention.

The invention claimed is:

1. A data processing method of simulating changes to categorical features of a subject, the method comprising:
    receiving a current categorical feature set for the subject, the current categorical feature set for the subject comprising a plurality of categorical features for the subject, each categorical feature indicating a category from a plurality of possible categories into which the subject falls,
    inputting categorical features from the current categorical feature set for the subject into a set of trained machine learning models, each trained machine learning model of the set of trained machine learning model being configured to predict a respective outcome value for the subject from one or more of the categorical features for the subject, and thereby generating a set of current predicted outcome values for the subject;
    generating a plurality of simulated categorical features sets for the subject by varying respective categorical features for the subject;
    inputting categorical features from the simulated categorical feature sets for the subject into the set of trained machine learning models, and thereby generating a plurality of simulated sets of predicted outcome values for the subject; and
    storing a predicted outcome dataset for the subject, the predicted outcome dataset comprising the set of current predicted outcome values for the subject and the plurality of simulated sets of predicted outcome values for the subject.

2. A data processing method of simulating impact of changes to categorical features of a plurality of subjects, the method comprising:
    performing the method according to claim 1 for a plurality of subjects;
    for a target outcome and a target categorical feature, determining an average current outcome value from the current predicted outcome values for the target outcome corresponding to respective subjects, determining a minimum average outcome value from a lowest value of the target outcome for each respective subject in a simulated set of predicted outcome values of the plurality of simulated sets of predicted outcome values corresponding to the target categorical feature, and determining a maximum average outcome value from a highest value of the target outcome for each respective subject in a simulated set of predicted outcome values of the plurality of simulated sets of predicted outcome values corresponding to the target categorical feature;
    calculating a potential impact of the target categorical feature on the target outcome from the maximum average outcome value and the minimum average outcome value;
    calculating an actual impact of the target categorical feature on the target outcome from the average current outcome value and the minimum average outcome value; and
    displaying an indication of the potential impact of the target categorical feature on the target outcome and an indication of the actual impact of the target categorical feature on the target outcome.

3. A data processing method according to claim 2, wherein the indication of the potential impact of the target categorical feature on the target outcome and the indication of the actual impact of the target categorical feature on the target outcome are displayed on a single chart.

4. A data processing method according to claim 2, wherein the indication of the potential impact of the target categorical feature on the target outcome is a ratio of the maximum average outcome value to the minimum average outcome value and the indication of the actual impact of the target categorical feature on the target outcome is a ratio of the average current outcome value to the minimum average outcome value or a ratio of the maximum average outcome value to the average current outcome value.

5. A data processing method according to claim 2, wherein the indication of the potential impact of the target categorical feature on the target outcome is a logarithm of a ratio of the maximum average outcome value to the minimum average outcome value and the indication of the actual impact of the target categorical feature on the target outcome is a logarithm of a ratio of the average current outcome value to the minimum average outcome value or a logarithm of a ratio of the maximum average outcome value to the average current outcome value.

6. A data processing method according to claim 2, further comprising receiving an input indicating a selection of subjects and wherein the average current outcome value, the minimum average outcome value, and the maximum average outcome value are determined for the selection of subjects.

7. A non-transitory computer readable medium storing processor executable instructions which when executed on a processor cause the processor to carry out a method according to claim 1.

8. A data processing method according to claim 2, wherein the method is carried out for a plurality of target categorical features.

9. A data processing method according to claim 8, further comprising:
    calculating a group potential impact for a group of target categorical features on the target outcome from respective potential impacts of the target categorical features making up the group on the target outcome; and
    calculating a group actual impact for the group of target categorical features on the target outcome from the respective actual impacts of the target categorical features making up the group on the target outcome; and displaying an indication of the group potential impact and the group actual impact.

10. A data processing method of simulating changes to a categorical feature of a plurality of subjects, the method comprising:
receiving current categorical feature sets for each of a plurality of subjects, each current categorical feature set comprising a plurality of categorical features for a respective subject, each categorical feature indicating a category from a plurality of possible categories into which the respective subject falls;
determining a current categorical feature distribution for a target categorical feature for the plurality of subjects, the current categorical feature distribution indicating a fraction of subjects falling into each category of the plurality of possible categories for the target categorical feature;
inputting categorical features comprising the target categorical feature from the current categorical feature sets into a trained machine learning model configured to predict an outcome value for each subject from one or more of the categorical features for the subject, and thereby generating a current predicted outcome value for each subject;
generating a plurality of simulated categorical feature sets for each subject by varying the target categorical feature;
inputting categorical features from the simulated categorical feature sets into the trained machine learning model, and thereby generating a plurality of simulated sets of predicted outcome values,
generating an aggregated simulated predicted outcome dataset from the plurality of simulated sets of predicted outcome values indicating an average predicted outcome for each possible variation in the target categorical feature;
receiving an indication of a simulation target;
determining a categorical feature distribution movement transformation from the current categorical feature distribution to a simulation categorical feature distribution which corresponds to a simulation outcome;
determining a simulation result based on one or more of the simulation categorical feature distribution or the simulation outcome; and
outputting an indication of the simulation result.

11. A data processing method according to claim 10, wherein the indication of the simulation target comprises an indication of a target outcome value, the simulation outcome is the target outcome values and the simulation result is the simulation categorical feature distribution.

12. A data processing method according to claim 10, wherein the indication of the simulation target comprises an indication of a target distribution of categorical feature values, the simulation categorical feature distribution is the target distribution of categorical features and the simulation result is the simulation outcome.

13. A data processing method according to claim 12, wherein determining the categorical feature distribution movement transformation comprises determining a distribution movement transformation that gives a maximal simulated value, determining a distribution movement transformation that gives a minimal simulated value, determining a similarity measure between the simulation categorical feature distribution and each of a distribution resulting from applying the distribution movement transformation that gives a maximal simulated value to the current categorical feature distribution, the distribution movement transformation that gives a minimal simulated value to the current categorical feature distribution, and a unitary transformation to the current categorical feature distribution and thereby determining corresponding weights for the distribution movement transformation that gives a maximal simulated value, the distribution movement transformation that gives a minimal simulated value, and the unitary transformation.

14. A data processing method according to claim 13, wherein the similarity measure is a cosine similarity measure.

15. A data processing system for simulating changes to categorical features of a subject, the data processing system comprising a processor and a data storage device storing computer program instructions operable to cause the processor to:
receive a current categorical feature set for the subject, the current categorical feature set for the subject comprising a plurality of categorical features for the subject, each categorical feature indicating a category from a plurality of possible categories into which the subject falls;
input categorical features from the current categorical feature set for the subject into a set of trained machine learning models, each trained machine learning model of the set of trained machine learning model being configured to predict a respective outcome value for the subject from one or more of the categorical features for the subject, and thereby generating a set of current predicted outcome values for the subject;
generate a plurality of simulated categorical features sets for the subject by varying respective categorical features for the subject;
input categorical features from the plurality of simulated categorical feature sets for the subject into the set of trained machine learning models, and thereby generating a plurality of simulated sets of predicted outcome values for the subject; and
store a predicted outcome dataset for the subject, the predicted outcome dataset comprising the set of current predicted outcome values for the subject and the plurality of simulated sets of predicted outcome values for the subject.

16. A data processing system according to claim 15, wherein the data storage device further stores computer program instructions operable to cause the processor to:
for a target outcome and a target categorical feature, determine an average current outcome value from the current predicted outcome values for the target outcome corresponding to respective subjects, determining a minimum average outcome value from a lowest value of the target outcome for each respective subject in a simulated set of predicted outcome values of the plurality of simulated sets of predicted outcome values corresponding to the target categorical feature, and determining a maximum average outcome value from a highest value of the target outcome for each respective subject in a simulated set of predicted outcome values of the plurality of simulated sets of predicted outcome values corresponding to the target categorical feature;
calculate a potential impact of the target categorical feature on the target outcome from the maximum average outcome value and the minimum average outcome value;
calculate an actual impact of the target categorical feature on the target outcome from the average current outcome value and the minimum average outcome value; and display an indication of the potential impact of the target categorical feature on the target outcome and an indication of the actual impact of the target categorical feature on the target outcome.

17. A data processing system according to claim 16, wherein the indication of the potential impact of the target categorical feature on the target outcome and the indication of the actual impact of the target categorical feature on the target outcome are displayed on a single chart.

18. A data processing system according to claim 16, wherein the indication of the potential impact of the target categorical feature on the target outcome is a ratio of the maximum average outcome value to the minimum average outcome value and the indication of the actual impact of the target categorical feature on the target outcome is a ratio of the average current outcome value to the minimum average outcome value or a ratio of the maximum average outcome value to the average current outcome value.

19. A data processing system according to claim 16, wherein the indication of the potential impact of the target categorical feature on the target outcome is a logarithm of a ratio of the maximum average outcome value to the minimum average outcome value and the indication of the actual impact of the target categorical feature on the target outcome is a logarithm of a ratio of the average current outcome value to the minimum average outcome value or a logarithm of a ratio of the maximum average outcome value to the average current outcome value.

20. A data processing system according to claim 16, wherein the data storage device further stores computer program instructions operable to cause the processor to: receive an input indicating a selection of subjects and wherein the average current outcome value, the minimum average outcome value, and the maximum average outcome value are determined for the selection of subjects.

21. A data processing system according to claim 16, wherein the data storage device further stores computer program instructions operable to cause the processor to: simulate changes to a plurality of target categorical features.

22. A data processing system according to claim 21, wherein the data storage device further stores computer program instructions operable to cause the processor to: calculate a group potential impact for a group of target categorical features on the target outcome from the respective potential impacts of the target categorical features making up the group on the target outcome; and
calculate a group actual impact for the group of target categorical features on the target outcome from the respective actual impacts of the target categorical features making up the group on the target outcome; and
display an indication of the group potential impact and the group actual impact.

23. A data processing system for simulating changes to a categorical feature of a plurality of subjects, the data processing system comprising a processor and a data storage device storing computer program instructions operable to cause the processor to:
receive current categorical feature sets for each of a plurality of subjects, each current categorical feature set comprising a plurality of categorical features for a respective subject, each categorical feature indicating a category from a plurality of possible categories into which the respective subject falls;
determine a current categorical feature distribution for a target categorical feature for the plurality of subjects, the current categorical feature distribution indicating a fraction of subjects falling into each category of the plurality of possible categories for the target categorical feature;
input categorical features comprising the target categorical feature from the current categorical feature sets into a trained machine learning model configured to predict an outcome value for each subject from one or more of the categorical features for the subject, and thereby generating a current predicted outcome value for each subject;
generate a plurality of simulated categorical feature sets for each subject by varying the target categorical feature;
input categorical features from the simulated categorical feature sets into the trained machine learning model, and thereby generating a plurality of simulated sets of predicted outcome values;
generate an aggregated simulated predicted outcome dataset from the plurality of simulated sets of predicted outcome values indicating the average predicted outcome for each possible variation in the target categorical feature;
receive an indication of a simulation target;
determining a categorical feature distribution movement transformation from the current categorical feature distribution to a simulation categorical feature distribution which corresponds to a simulation outcome;
determine a simulation result based on the simulation categorical feature distribution and/or the simulation outcome; and
output an indication of the simulation result.

24. A data processing system according to claim 23, wherein the indication of the simulation target comprises an indication of a target distribution of categorical feature values, the simulation categorical feature distribution is the target distribution of categorical features and the simulation result is the simulation outcome.

25. A data processing system according to claim 23, wherein the indication of the simulation target comprises an indication of a target outcome value, the simulation outcome is the target outcome values and the simulation result is the simulation categorical feature distribution.

26. A data processing system according to claim 23, wherein the data storage device further stores computer program instructions operable to cause the processor to: determine the categorical feature distribution movement transformation by determining a distribution movement transformation that gives a maximal simulated value, determining a distribution movement transformation that gives a minimal simulated value, determining a similarity measure between the simulation categorical feature distribution and each of a distribution resulting from applying the distribution movement transformation that gives a maximal simulated value to the current categorical feature distribution, the distribution movement transformation that gives a minimal simulated value to the current categorical feature distribution, and a unitary transformation to the current categorical feature distribution and thereby determining corresponding weights for the distribution movement transformation that gives a maximal simulated value, the distribution movement transformation that gives a minimal simulated value, and the unitary transformation.

27. A data processing system according to claim 26, wherein the similarity measure is a cosine similarity measure.

* * * * *